(12) United States Patent
Robichaud et al.

(10) Patent No.: US 6,824,999 B1
(45) Date of Patent: Nov. 30, 2004

(54) DETECTION OF ANTIBODIES TO GANGLIOSIDES USING SOLID-PHASE REACTANTS COATED WITH CARBONYL GROUPS

(75) Inventors: Normand J. Robichaud, Leominster, MA (US); Louis P. Kertiles, Petersham, MA (US)

(73) Assignee: Athena Diagnostics, Inc., Worcester, MA (US)

( * ) Notice: Subject to any disclaimer, the term of this patent is extended or adjusted under 35 U.S.C. 154(b) by 0 days.

(21) Appl. No.: 09/565,837

(22) Filed: May 5, 2000

(51) Int. Cl.[7] .............................................. G01N 33/53
(52) U.S. Cl. ...................................................... 435/7.92
(58) Field of Search ............................... 435/7.92, 967, 435/975

(56) References Cited

U.S. PATENT DOCUMENTS

| | | | |
|---|---|---|---|
| 5,443,952 A | 8/1995 | Pestronk | |
| 6,077,681 A | * 6/2000 | Pestronk | .................... 435/7.92 |
| 6,352,831 B1 | 3/2002 | Buschard et al. | |
| 6,448,023 B1 | 9/2002 | Skinner et al. | |

FOREIGN PATENT DOCUMENTS

WO    WO 98/35233 A1    8/1998

OTHER PUBLICATIONS

Van den Berg, L., et al., "Anti–MAG and Anti–SGPG Antibodies in Neuropathy," *Muscle Nerve*, 19(5):637–643 (1996).

Miyatani, N., et al., "Glycosphingolipids in the Cerebrospinal Fluid of Patients with Multiple Sclerosis," *Mol. Chem. Neuropathol.*, 13(3):205–216 (1990).

Ilyas, A.A., et al., "Antibodies to Sulfated Glycolipids in Gillain–Barre Syndrome, " *J. Neurol. Sci.*, 105(1):108–117 (1991).

Yuki, N., et al., "Correlation Between cytomegalovirus Infection and IgM Anti–MAG/SGPG Antibody Associated Neuropathy," *Ann. Neurol.*, 44(3):408–410 (1998).

Yuki, N., et al., "Autoantibodies to Peripheral Nerve Glycosphingolipids SPG, SLPG, and SGPG in Guillain–Barre Syndrome and Chronic Inflammatory Demyelinating Polyneuropathy," *J. Neuroimmunol.*, 70(1):1–6 (1996).

Hauttecoeur, B., et al., "Reactivity of Human Monoclonal IgM with Nerve Glycosphingolipids," *Clin. Exp. Immunol.*, 80(2):181–185 (1990).

Younes–Chennoufi, B.A., et al., "Anti–sulfoglucuronyl Paragloboside IgM Antibodies in Amyotrophic Lateral Sclerosis," *J. Neuroimmunol.*, 57(1–2):111–115 (1995).

Lauritzen, E., et al., "Peptide dot immunoassay and immunoblotting: Electroblotting from aluminum thin–layer chromatography plates and isoelectric focusing gels to activated nitrocellulose," *Electrophoresis*, 14:852–859 (1993).

Voet, D. and Voet, J., *Biochemistry*, Chapter 11, Lipids and Membranes: 277. John Wiley & Sons.

Adams, D. et al.,"Motor conduction block and high titres of anti–GM1 ganglioside antibodies: pathological evidence of a motor neuropathy in a patient with lower motor neuron syndrome," *J. Neurol. Neurosurg. Psychiatry*, 56:982–987 (1993).

Kornberg, A.J. and Pestronk, A., "Chronic Motor Neuropathies: Diagnosis, Therapy, and Pathogenesis," *Ann. Neurol.* 37:S43–S50 (1995).

Kornberg, A.J. and Pestronk, A., "The Clinical and Diagnostic Role of Anti–$GM_1$ Antibody Testing," *Muscle & Nerve* 17:100–104 (1994).

Sadiq, S.A. et al.,"The spectrum of neurologic disease associated with anti–$GM_1$ antibodies," *Neurology* 40:1067–1072 (1990).

Adams, D. et al., "Predictive value of anti–$GM_1$ ganglioside antibodies in neuromuscular diseases: a study of 180 sera," *Neuroimmunology* 32:223–230 (1991).

Taylor, B.V. et al.,"The sensitivity and specificity of anti–$GM_1$ antibody testing," *Neurology* 47(4):951–955 (1996).

Sindern, E. et al.,"Serum antibodies to GM1 and GM3–gangliosides in systemic lupus erythematosus with chronic inflammatory demyelinating polyradiculoneuropathy," *Acta. Neurol. Scand.* 83:399–402 (1991).

Yuri, N. et al.,"Frequent presence of anti–$G_{Q1b}$ antibody in Fisher's syndrome," *Neurology* 43:414–417 (1993).

Katsuhiko, K. et al.,"Guillain–Barré syndrome associated with IgG anti–GM1b antibody subsequent to *Mycoplasma pneumoniae* infection," *J. Neurol. Sci.* 156:99–101 (1998).

Pestronk, A.et al., "Lower Motor Neuron Syndromes Defined by Patterns of Weakness, Nerve Conduction Abnormalities, and High Titers of Antiglycolipid Antibodies," *Ann. Neurol.* 27:316–326 (1990).

Younes–Chennoufi, A.B. et al., "Antiganglioside antibodies in motor–neuron diseases and peripheral neuropathies: study by ELISA technique and immunodetection on thin–layer chromatography," *Neurochem. Inv.* 20(3):353–357 (1992).

Ravindranath, M.H. et al., "Factors affecting the fine specificity and sensitivity of serum antiganglioside antibodies in ELISA," *J. Immunological Methods* 169:257–272 (1994).

* cited by examiner

*Primary Examiner*—Patrick J. Nolan
(74) *Attorney, Agent, or Firm*—Hamilton, Brook, Smith & Reynolds, P.C.

(57) ABSTRACT

Methods of detecting antibodies to one or more ganglioside (s) of interest in a sample are disclosed which comprise using a solid-phase reactant having carbonyl groups attached thereon, and the ganglioside(s) of interest linked to the solid-phase reactant by an amide bond between an amino group of the ganglioside of interest and a carbonyl group attached to the solid-phase reactant. The methods of detecting antibodies to ganglioside(s) of interest can be used in methods of diagnosing neuropathies in an individual.

19 Claims, 1 Drawing Sheet

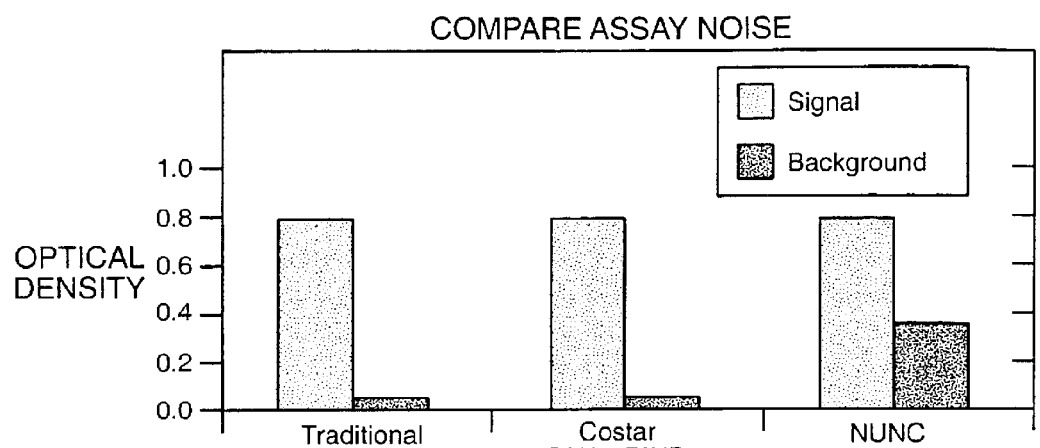
FIG._1
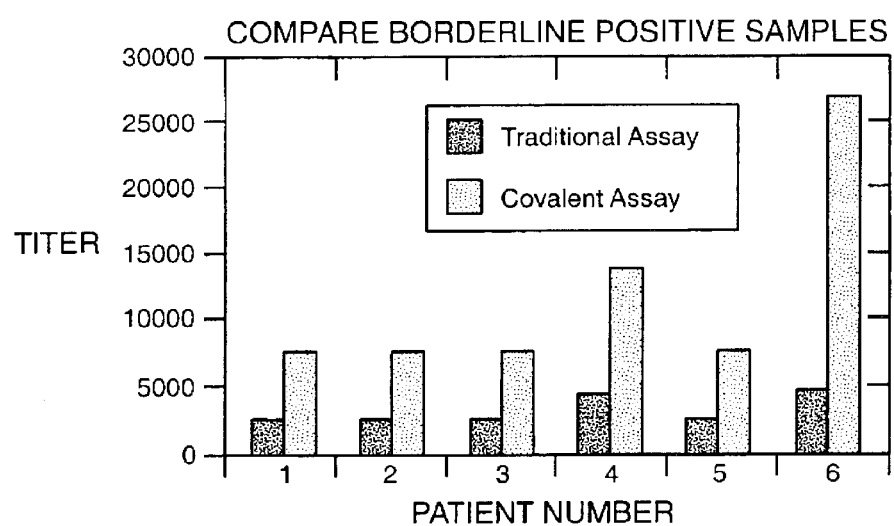
FIG._2

DETECTION OF ANTIBODIES TO GANGLIOSIDES USING SOLID-PHASE REACTANTS COATED WITH CARBONYL GROUPS

BACKGROUND OF THE INVENTION

Antibodies to gangliosides have been implicated in many different autoimmune neuropathies. For example, serum IgM antibodies to GM ganglioside have been found in a patient with lower motor neuron syndrome (Adams, D. et al., *J. Neurol. Neurosurg. Psychiatry* 56:982–987 (1993)), and are common in multifocal motor neuropathy (Kornberg, A. J. and Pestronk, A., *Ann. Neurol.* 37:S43–S50 (1995); Kornberg, A. J. and Pestronk, A., *Muscle Nerve* 17:100–104 (1994); Cetacea, S. A. et al., *Neurology* 40:1067–1072 (1990); Adams, D. et al., *Neuroimmunology* 32:223–230 (1991); Taylor, B. V. et al., *Neurology* 46:951–955 (1996)). Autoantibodies against GM- and GM-gangliosides have been found in conjunction with chronic idiopathic demyelinating polyneuropathy (CID) in conjunction with systemic lupus erythematosus (SLE) (Sindem, E. et al., *Acta. Neurol. Scand.* 83:399–402 (1991)). Anti-GQ1B ganglioside antibodies were identified in patients with Fisher's syndrome (Yuri, N. et al., *Neurology* 43:414–417 (1993)). Sera from patients with Gillian-Barr. syndrome has been found to have antibodies to various gangliosides, including antibodies to GM1B ganglioside (see, e.g., Cathouse, K. et al., *J. Neurol. Sci.* 156:99–101 (1998)).

Enzyme-linked immunosorbent assays (ELISA) have been used for identification of antibodies to gangliosides (see, for example, identification of GM ganglioside in Pestronk, A. et al. *Ann. Neurol.* 27:316–326 (1990)); U.S. Pat. No. 5,443,952; Aenaeus-Kanaf, A. B. et al., *Neurochem. Inv.* 20(3):353–357 (1992)). However, high background values frequently interfere with accurate assessment of the amount of anti-ganglioside antibodies (Ravindranath, MH et al., *J. Immunological Methods* 169:257–272 (1994)). Reliable measurement of anti-ganglioside antibodies is critical for correct diagnosis of neuropathies, particularly motor neuropathies.

SUMMARY OF THE INVENTION

The present invention pertains to methods of determining, in a test sample, the amount of antibodies directed against a specific nervous system antigen or antigens, using a modified solid-phase reactant. The method utilizes a solid-phase reactant, such as a microtiter plate, that is modified with carbonyl groups attached to its surface. One or more gangliosides of interest (e.g., asialo GM ganglioside, GM1 ganglioside, GM2 ganglioside, GM3 ganglioside, GD1a ganglioside, GD1B ganglioside, GD2 ganglioside, GD3 ganglioside, GQ1b ganglioside, and/or GT1b ganglioside) are linked to the modified solid-phase reactant by an amide bond between an amino group of the ganglioside and a carbonyl group attached to the solid-phase reactant. One or more control antigens, such as other glycolipids, glycoproteins or carbohydrates, can also be attached on the surface of the modified solid-phase reactant. The modified solid-phase reactant having ganglioside(s) of interest linked thereon is contacted with a test sample, such as a test sample of a bodily fluid (e.g., blood, serum, cerebrospinal fluid, or urine) from an individual, under conditions such that any antibody to the ganglioside(s) of interest that may be present in the test sample can bind to the ganglioside(s) of interest linked to the modified solid-phase reactant. The amount of antibodies in the test sample to the ganglioside(s) of interest is then determined using standard methods, such as enzyme-linked immunosorbent assay (ELISA) or another appropriate solid-phase assay. If a control antigen is attached on the modified solid-phase reactant, the level of antibodies in the test sample to the control antigen, can also be determined using the same methods. Specific reactivity of antibodies to the ganglioside of interest is determined by the amount of antibody binding to the ganglioside of interest that is above the amount of antibody binding to the control antigen. The methods can be used for diagnosing a neuropathy in an individual. The amount of antibody to a ganglioside of interest in a test sample from the individual is determined using the methods. An amount of antibody to a ganglioside of interest that is greater, by an amount that is statistically significant, than the amount of antibody to the ganglioside of interest in a control sample, is indicative of the presence of the neuropathy. Alternatively, an amount of antibody to a ganglioside of interest that is equal to or greater than an established reference amount is indicative of the presence of the neuropathy.

The invention also pertains to test kits, containing modified solid-phase reactants, for use in the methods of the invention.

The high sensitivity and specificity of the methods can clarify the differential diagnosis of neuropathies and reduce the need for time-consuming and expensive electrophysiological evaluation. Furthermore, a modified solid-phase reactant having carbonyl groups attached to its surface allows the use of a smaller amount of ganglioside than the amount which would otherwise be necessary to perform similar assays with a solid-phase reactant not having this modification. In addition, a modified solid-phase reactant having carbonyl groups attached to its surface can be coated with a ganglioside of interest without a need for toxic solvents; the coating is not affected by humidity, and yields consistent and reproducible assay results.

BRIEF DESCRIPTION OF THE DRAWINGS

FIG. 1 is a graphic depiction of a comparison of signal to background noise of several types of solid phase reactants. Black, signal; grey, background.

FIG. 2 is a graphic depiction of a comparison of sensitivity of traditional solid phase reactants to modified solid phase reactants in detecting titers of antibodies to ganglioside. Grey, traditional solid phase reactant; black, modified solid phase reactant.

DETAILED DESCRIPTION OF THE INVENTION

The invention described herein relates to methods of determining the amount of antibodies to one or more ganglioside(s) of interest in a sample. The invention further pertains to methods of diagnosing neuropathies (e.g., multifocal motor neuropathy) in an individual by determining the amount of antibodies to one or more ganglioside(s) of interest in a sample from the individual. Applicant has discovered that significantly increased sensitivity for antibodies to certain gangliosides can be achieved by conducting an enzyme-linked immunosorbent assay (ELISA) using microtiter plates that are modified with carbonyl groups, allowing amide linkage of gangliosides to the plates.

As a result of this discovery, highly sensitive and specific methods of determining the presence or absence, and the amount, of antibody to one or more ganglioside(s) of interest in a sample are now available. In the methods, a modified solid-phase reactant is used. The term, "solid-phase reactant", as used herein, refers to a solid medium, such as a microtiter plate, a membrane (e.g., nitrocellulose), a bead, a dipstick, a thin-layer chromatographic plate, or other solid medium. In a preferred embodiment, the solid-phase reactant is a microtiter plate that can be used in a solid-phase immunoassay, such as an enzyme-linked immunosorbent assay. The solid-phase reactant is modified such that carbonyl groups are grafted into the reactant. As a result of the presence of the carbonyl groups, certain antigens, such as glycolipids, glycoproteins, carbohydrates, or other antigens containing amino groups, can be linked on the surface of the solid-phase reactant by an amide bond between the carbonyl group on the solid-phase reactant and the amino group of the antigen. A representative solid-phase reactant that allows linkage of antigens on its surface in this manner is the Co-star DNA-BIND covalent plate (Co-star, Corning, N.Y.). A solid-phase reactant that has carbonyl groups attached thereon and therefore has the ability to allow amide bond linkage of antigens onto its surface is referred to herein as a "modified solid-phase reactant".

One or more ganglioside(s) of interest is linked to the modified solid-phase reactant. A ganglioside of interest that is "linked" or "attached" to the modified solid-phase reactant is a ganglioside that has formed an amide bond between an amino group of the ganglioside and the carbonyl group attached to the modified solid-phase reactant. Representative gangliosides include asialo GM ganglioside, GM1 ganglioside, GM2 ganglioside, GM3 ganglioside, GD1a ganglioside, GD1B ganglioside, GD2 ganglioside, GD3 ganglioside, GQ1b ganglioside, and GT1b ganglioside. One type of ganglioside can be used; alternatively, more than one type of ganglioside can be linked to the covalent-linkage solid-phase reactant. As used herein, a solid-phase reactant having "at least one" ganglioside of interest linked thereon may have only one type of ganglioside of interest thereon, or may also have more than one type of ganglioside of interest thereon. In a preferred embodiment, asialo GM ganglioside; GM1 ganglioside; and GD1b ganglioside are linked to the modified solid-phase reactant. A representative method of linking uses the ganglioside of interest reconstituted in methanol and diluted into phosphate buffered saline. EDAC (1-ethyl-3-(3-diethylaminopropyl)carbodiimide) can also be included, if desired; for example, in one embodiment, if the ganglioside of interest is GD1B ganglioside, EDAC is included in the solution containing the ganglioside; the solution containing the ganglioside is then allowed to coat the modified solid-phase reactant. Because the modified solid-phase reactant contains carbonyl groups, amino groups present on the gangliosides form amide bonds with the carbonyl groups when exposed to the carbonyl groups on the modified solid-phase reactant. A modified solid-phase reactant on which one or more ganglioside(s) is attached is referred to herein as a "ganglioside modified solid-phase reactant".

A control antigen, such as another ganglioside, or a glycolipid, glycoprotein or carbohydrate, can also be attached to the modified solid-phase reactant. More than one control antigen can be used. A control antigen can be identified, for example, by evaluation of a number of samples from individuals having known disease states. "Specific binding" is indicated by statistically demonstrated binding of antibody in the sample to the antigen of interest, relative to the clinical status (disease state) of the samples (e.g., binding, in a statistically significant number of samples from individuals having a particular disease state, of antibody to the particular antigen). A lack of binding to a particular antigen by a sample from an individual having a known clinical status is generally accepted as being indicative of a non-reactive (control) antigen.

The control antigen(s) can be attached to the modified solid-phase reactant using methods similar to those used to coat the ganglioside(s) of interest onto the modified solid-phase reactant. The control antigen is usually attached to the modified solid-phase reactant at a different location than the ganglioside(s) of interest. For example, if the solid-phase reactant is a microtiter plate, a ganglioside of interest can be attached to certain wells of the plate, and the control antigen can be attached to other wells of the plate. In another example, if more than one ganglioside of interest is attached to the plate, the control antigen is attached to certain wells of the plate; a first ganglioside of interest is attached to other wells of the plate; a second ganglioside of interest is attached to different wells of the plate from either the control antigen or the first ganglioside of interest, etc. Alternatively, the control antigen can be attached to a separate solid-phase reactant, the separate solid-phase reactant being the same type of solid-phase reactant as that onto which the ganglioside(s) of interest is coated. It is intended that the term, "ganglioside modified solid-phase reactant", refers to those modified solid-phase reactants having one or more ganglioside(s) of interest attached thereon, as well as to those modified covalent-linkage solid-phase reactants having one or more ganglioside(s) of interest attached thereon as well as one or more control antigens attached at a different location thereon. The term, "control antigen solid-phase reactant" is used to refer to a solid-phase reactant having solely control antigen(s) attached thereto.

The ganglioside modified solid-phase reactant (and control antigen solid-phase reactant, if used) is used in an assay to determine the amount of antibody to one or more ganglioside(s) of interest in a test sample. The test sample to be assayed for the amount of antibody to a ganglioside of interest can be a sample of bodily fluid or tissue from an individual For example, the test sample can comprise blood, serum, cerebrospinal fluid, urine, nasal secretion, saliva, or any other bodily fluid or tissue. Alternatively, the test sample can comprise antibodies, and particularly IgM, IgG and/or IgA antibodies, that have been isolated from a sample of bodily fluid or tissue from the individual. In a preferred embodiment, the test sample is a serum sample from an individual suspected of having a neuropathy.

To determine the amount of anti-ganglioside antibody in a test sample, the ganglioside modified solid-phase reactant is contacted with the test sample. A ganglioside modified solid-phase reactant that has been contacted with a test sample is referred to herein as a "contacted ganglioside modified solid-phase reactant." The contacted ganglioside modified solid-phase reactant is maintained under appropriate conditions to allow binding of any antibody to the ganglioside(s) of interest that may be present in the test sample, to the ganglioside(s) of interest that is attached to the solid-phase reactant. The term, "antibody to a ganglioside of interest" refers to an antibody or antibodies that preferentially binds to the ganglioside of interest. For example, an antibody to a ganglioside of interest preferentially binds to the ganglioside of interest in an amount that is greater than to control antigens (e.g., glycolipids, glycoproteins or carbohydrates), and/or in an amount that is greater than to other gangliosides, by an amount that is statistically significant. The antibody to the ganglioside of interest may bind to a ganglioside that is in a lipid environment (e.g., GM1 ganglioside in a lipid mixture of GM1 ganglioside, galactocerebroside, and cholesterol (GGC)), and/or may bind to a ganglioside that is isolated (e.g., not in a lipid environment).

The amount of antibody to the ganglioside(s) of interest in the test sample, if any, that has bound to the ganglioside(s) of interest on the modified solid-phase reactant is determined. The amount is determined separately for each ganglioside of interest. It is expected that an antibody will specifically interact with a ganglioside of interest; that is, an antibody will interact preferentially with one ganglioside of interest, and not to another ganglioside of interest.

The amount of antibody can be determined by a variety of methods using standard techniques, including enzyme-linked immunosorbent assay (ELISA), solid phase radioimmunoassay, or other solid phase immunoassays (see Ausubel, F. M. et al., eds., Current Protocols in Molecular Biology, John Wiley & Sons, 1996, especially units 11.2 (ELISA) and 11.16 (Determination of Specific Antibody Titer); the entire teachings of this reference are incorporated herein by reference). In a typical solid-phase immunoassay, the amount of antibody bound to the ganglioside of interest attached to the modified solid-phase reactant is determined using a developing reagent, such as a detection antibody that binds to the antibody to the ganglioside of interest. The detection antibody can be linked or conjugated to another molecule, such as an enzyme or fluorophore, to facilitate detection. Alternatively, the detection antibody is iodinated. If more than one ganglioside of interest is used, different detection antibodies can be used to detect each antibody to each ganglioside of interest. For example, a detection antibody that binds to an antibody to one ganglioside of interest can be conjugated to a first fluorophore, and a detection antibody that binds to an antibody to a second ganglioside of interest can be conjugated to a second fluorophore that is distinguishable from the first fluorophore. Alternatively, if the same detection reagent is used, the different gangliosides of interest can be attached to the modified solid-phase reactant at a different, identifiable location, such that the presence of a detection reagent at a particular location corresponds to the presence of antibodies to the ganglioside of interest attached to the modified solid-phase reactant at that location.

In a preferred embodiment, an ELISA assay is performed, using as a developing reagent a detection antibody that is linked to an enzyme, such as horseradish peroxidase. The contacted ganglioside modified solid phase-reactant is incubated with the developing reagent, forming a developed, contacted solid-phase reactant. Subsequently, a substrate of the enzyme is added to the developed, contacted solid-phase reactant, and the amount of activity of the enzyme on its substrate (e.g., the amount of hydrolysis of the substrate) is measured by an appropriate means, such as by measuring optical density.

Titers of antibodies to the ganglioside(s) of interest can be calculated from the amount of detector antibody bound to the antibodies to the ganglioside of interest, using standard conversion algorithms. For example, if the developing reagent comprises horseradish peroxidase, titers of antibody can be calculated as set forth in Pestronk et al. (Ann. Neurol. 2.7:316–326 (1990)).

If a control antigen is attached to the modified solid-phase reactant, titers of antibody binding to the control antigen are subtracted from the titers of antibody binding to the ganglioside of interest. The difference between the titer of antibody binding to the ganglioside of interest and the titer of antibody binding to the control antigen(s) is indicative of the specific (selective) binding of the antibody to the ganglioside of interest. If the control antigen is attached to a separate modified solid-phase reactant, the control antigen modified solid-phase reactant is contacted with the test sample in the same manner as the ganglioside modified solid-phase reactant and maintained under the same conditions. The amount of antibody to the control antigen is determined by the same method as is used to determine the amount of antibody to the ganglioside of interest.

Neuropathies, particularly immune-mediated neuropathies, can be diagnosed using these methods of determining the amount of antibody to a ganglioside of interest. To diagnose these neuropathies, the test sample is a sample from an individual to be tested for the presence of a neuropathy. The amount of antibody to a ganglioside(s) of interest in the test sample is compared with the amount of comparable antibody to the ganglioside(s) of interest in at least one comparable control sample (i.e., a sample of the same type(s) of antibody (IgM, IgG, and/or IgA) from an individual who is not afflicted by a neuropathy). The control sample can be a sample from any individual who is not afflicted with a neuropathy; it is not necessary that the control sample be from an individual who is free of disease. For example, the control sample can be a sample from an individual who has amyotrophic lateral sclerosis, or systemic immune disorders. A "comparable" normal sample is a sample of the same type of body fluid or tissue as the test sample; alternatively, if the test sample is IgM antibodies isolated from a sample of fluid or tissue, the comparable normal or control sample is a sample of IgM antibodies isolated from the same type of bodily fluid or tissue. More than one control sample can be used. The presence of an amount of specific (selective) ganglioside antibody binding in the test sample that is greater, by an amount that is statistically significant, than the amount of specific (selective) ganglioside antibody binding in a comparable control sample, correlates with a diagnosis of the neuropathy.

Alternatively, the amount of antibody to a ganglioside(s) of interest in the test sample can be compared with a "reference amount". A reference amount, as used herein, is an amount (e.g., a titer) of antibody to a ganglioside of interest which has been previously determined to correlate with a particular disease state. For example, a reference amount can be determined by assessing the amount of antibody to ganglioside(s) of interest in a set of samples from individuals having known diseases (e.g., neuropathies), as well as comparable control samples as described above, and determining what amount of antibody correlates with disease. An amount of antibody to a ganglioside(s) of interest in the test sample that is equal to, or greater than, the reference amount, correlates with a diagnosis of the neuropathy.

The present invention also includes kits to be used in methods of the invention. Kits can include the following components: (1) a modified solid-phase reactant having carbonyl groups, and also having one or more ganglioside(s) of interest attached thereto by amide bonds; and (2) labeled detector antibody that binds to the antibody to the ganglioside(s) of interest. The detector antibody can be specific for the type of antibody (e.g., IgM, IgG or IgA) Detector antibody can comprise an antibody bound to a detectable agent, such as an enzyme, radioactive molecule, or fluorescent agent. If the detector antibody is bound to an enzyme that reacts with an added substrate to yield a colored product, such as horseradish peroxidase, the kit can also include the substrate.

The invention is now further illustrated by the following Exemplification.

EXEMPLIFICATION

Comparison of Antibody Titers Using a Variety of Enzyme-Linked Immunosorbent Assay (ELISA) Plates A comparison of background noise and antibody titers was made, using traditional (Falcon polystyrene) plates, plates modified with carbonyl groups allowing amide linkage of gangliosides to the plates (Co-star DNA-BIND plates), and plates modified with secondary amino groups on its surface (Nunc CovaLink plates, Nunc, Roskilde, Denmark).

Linking of Antigen to Covalent Plates

Antigen-coating solutions were prepared. For GD1b ganglioside, 1% EDAC in PBS (0.01 g EDAC per ml PBS) was used; for GM1 ganglioside and asialo ganglioside, PBS was used. Antigen stocks were prepared by reconstituting lyophilized antigen vials with methanol to a concentration of 1 mg/ml. An aliquot of the 1 mg/ml GD1b stock was diluted into 1% EDAC to make GD1b antigen coating solution at the desired concentration. Aliquots of the 1 mg/ml GM1 ganglioside and asialo ganglioside stocks were diluted in PBS to make the GM1 ganglioside and asialo ganglioside coating solutions at the desired concentrations.

Each plate required 5.5 ml of coating antigen solutions. Plates were removed from foil pouches just prior to use, avoiding direct light that could damage the plates. Antigen coating solution (100 ml/well) was added to rows A, B, E, and F; rows C, D, G and H were left un-coated as the antigen blank wells. Coated plates were incubated in the dark at 4° C. overnight. The coating solution was then aspirated, and the plates washed 3 times with 1% BSA. After the third wash, all plate wells were filled with 1% BSA, and the plates were blocked for at least 16 hours at 4° C. in the dark.

Sample Addition

A robot robotic automatic pipeting system was used to add diluted samples and controls to the plates. The plates were then incubated at 4° C. overnight in the dark.

Detection Antibody Probe and Colorimetric Reaction

Detection antibody (peroxidase conjugated goat anti-human IgG, IgM and IgA cocktail) was diluted in 1% BSA to the desired dilution, which was determined for each lot of antibody prior to use. Eleven ml of dilute detection antibody were used for each plate. Assay plates were aspirated and washed 6 times with 1% BSA, and then blotted. dilute detection antibody solution (100 ml/well) was added to all assay plates, and the plates were incubated in the dark at room temperature for 2 hours. Substrate solution was then prepared: 100 mg of OPD and 12 ml of 30% hydrogen peroxide were added to 100 ml of 0.1 M citric acid (pH 4.5) to form substrate solution (11 ml per assay plate). All assay plates were then aspirated and washed 6 times with 1% BSA, and then blotted. Substrate solution (100 ml/well) was added to all assay plates, which were then covered to avoid light exposure. Pleases were incubated at room temperature, and read approximately 20 minutes after addition of substrate at 405 nm until both positive controls reached the established minimum OD validated for the positive control in use.

Results

A comparison of the background noise of a variety of ELISA plates was performed. A positive clinical control was used to represent the signal, and the background was a BSA buffer blank (absence of sample). Results are shown in Table 1 and FIG. 1.

TABLE 1

Comparison of Background Noise with Different ELISA Plates

| Plate | Signal | Background |
| --- | --- | --- |
| Traditional | 0.81 | 0.05 |
| Co-star DNA-Bind | 0.82 | 0.05 |
| Nunc Covalink | 0.82 | 0.35 |

FIG. 1 demonstrates the results of the comparison of the signal to background noise of the traditional plate (Falcon polystyrene plate); the plate having carbonyl groups attached thereon (the Co-star DNA-BIND plate); and the plate having secondary amino groups on its surface (NUNC Coating plate, Nunc; Roskilde, Denmark). It can be seen that the plate having carbonyl groups exhibited low background noise compared to the other plates.

Sensitivity of the current methods was also assessed. Six samples previously run in a clinically validated GM1 ganglioside assay and found to have low positive anti-GM1 ganglioside antibody were used. Results are shown in Table 2 and FIG. 2.

TABLE 2

Comparison of Antibody Titers Obtained with Different Plates

| Patient Number | Traditional Plate (Falcon) Titer | Covalent Plate (Co-Star DNA BIND) Titer |
| --- | --- | --- |
| 1 | 1600 | 6400 |
| 2 | 1600 | 6400 |
| 3 | 1600 | 6400 |
| 4 | 3200 | 12800 |
| 5 | 1600 | 6400 |
| 6 | 3200 | 25600 |

FIG. 2 demonstrates the sensitivity of the current methods. The plate having carbonyl groups attached thereon yields a consistently higher titer for the same samples. The elevated signal obtained by performing an ELISA using the plate having carbonyl groups attached thereon diminishes "grey areas" (titers that are close to the reference amount, and are therefore considered "borderline"), and thereby decreases the number of questionable positive samples. Furthermore, the amount of ganglioside used on the plate having carbonyl groups attached thereon was half the amount on the traditional Falcon polystyrene plate.

Those skilled in the art will be able to recognize, or be able to ascertain, using no more than routine experimentation, many equivalents to the specific embodiments of the invention described herein. Such equivalents are intended to be encompassed by the following claims.

What is claimed is:

1. An improved method of determining in a test sample the amount of antibody to at least one ganglioside of interest, in which the amount of antibody is determined by performing an assay using a solid phase reactant, wherein the improvement comprises using a modified solid-phase reactant having carbonyl groups attached thereon and ganglioside of interest linked to the modified solid-phase reactant by an amide bond between an amino group of the ganglioside of interest and a carbonyl group attached to the modified solid-phase reactant.

2. The method of claim 1, comprising performing an enzyme-linked immunosorbent assay to determine the amount of antibody to the ganglioside of interest.

3. The method of claim 1, wherein the ganglioside of interest is selected from the group consisting of: asialo GM ganglioside, GM1 ganglioside, GM2 ganglioside, GM3 ganglioside, GD1a ganglioside, GD1B ganglioside, GD2 ganglioside, GD3 ganglioside, GQ1b ganglioside, and GT1b ganglioside.

4. The method of claim 1, wherein the amount of antibody to more than one ganglioside of interest is determined, and wherein each ganglioside of interest is linked to the modified solid-phase reactant by an amide bond between an amino group of the ganglioside of interest and a carbonyl group attached to the modified solid-phase reactant.

5. The method of claim 4, wherein the gangliosides of interest are each selected from the group consisting of: asialo GM ganglioside, GM1 ganglioside, GM2 ganglioside, GM3 ganglioside, GD1a ganglioside, GD1B ganglioside, GD2 ganglioside, GD3 ganglioside, GQ1b ganglioside, and GT1b ganglioside.

6. A method of determining in a test sample the amount of antibody to at least one ganglioside of interest, comprising the steps of:
   a) providing a ganglioside modified solid-phase reactant, the ganglioside modified solid-phase reactant comprising a modified solid-phase reactant having carbonyl groups attached thereon and the ganglioside of interest linked to the modified solid-phase reactant by an amide bond between an amino group of the ganglioside of interest and a carbonyl group attached to the modified solid-phase reactant;
   b) contacting the ganglioside modified solid-phase reactant with a test sample, thereby forming a contacted ganglioside modified solid-phase reactant;
   c) maintaining the contacted ganglioside modified solid-phase reactant under appropriate conditions to allow antibody to the ganglioside of interest, if present in the sample, to bind to the ganglioside of interest linked to the modified solid-phase reactant; and
   d) determining the amount of antibody to the ganglioside of interest that is bound to the ganglioside of interest linked to the modified solid-phase reactant.

7. The method of claim 6, wherein the ganglioside of interest is selected from the group consisting of: asialo GM ganglioside, GM1 ganglioside, GM2 ganglioside, GM3 ganglioside, GD1a ganglioside, GD1B ganglioside, GD2 ganglioside, GD3 ganglioside, GQ1b ganglioside, and GT1b ganglioside.

8. The method of claim 6, wherein the modified solid-phase reactant additionally comprises at least one control antigen attached to the modified solid-phase reactant.

9. The method of claim 8, wherein the control antigen is selected from the group consisting of: a glycolipid, a glycoprotein, and a carbohydrate.

10. The method of claim 6, wherein the solid-phase reactant is a microliter plate.

11. The method of claim 6, wherein the amount of antibody to the ganglioside of interest that is bound to the ganglioside of interest attached to the modified solid-phase reactant is determined by incubating the contacted ganglioside modified solid-phase reactant with a developing reagent.

12. The method of claim 11, wherein the developing reagent comprises a detection antibody that binds to antibody to the ganglioside of interest.

13. The method of claim 12, wherein the detection antibody is conjugated to an enzyme.

14. The method of claim 12, wherein the detection antibody is conjugated to a fluorophore.

15. The method of claim 12, wherein the detection antibody is iodinated.

16. A method of determining in a test sample the amount of antibody to more than one ganglioside of interest, comprising the steps of:
   a) providing a ganglioside modified solid-phase reactant, the ganglioside modified solid-phase reactant comprising a modified solid-phase reactant having carbonyl groups attached thereon and each ganglioside of interest linked to the modified solid-phase reactant by an amide bond between an amino group of each ganglioside of interest and a carbonyl group attached to the modified solid-phase reactant;
   b) contacting the ganglioside modified solid-phase reactant with a test sample, thereby forming a contacted ganglioside modified solid-phase reactant;
   c) maintaining the contacted ganglioside modified solid-phase reactant under appropriate conditions to allow antibody to each ganglioside of interest, if present in the sample, to bind to a ganglioside of interest linked to the modified solid-phase reactant; and
   d) determining the amount of antibody to each ganglioside of interest that is bound to the ganglioside of interest linked to the modified solid-phase reactant.

17. The method of claim 16, wherein the gangliosides of interest are each selected from the group consisting of: asialo GM ganglioside, GM1 ganglioside, GM2 ganglioside, GM3 ganglioside, GD1a ganglioside, GD1B ganglioside, GD2 ganglioside, GD3 ganglioside, GQ1b ganglioside, and GT1b ganglioside.

18. A method of determining in a test sample the amount of antibody specific to at least one ganglioside of interest, comprising the steps of:
   1) providing a ganglioside modified solid-phase reactant, the ganglioside modified solid-phase reactant comprising a modified solid-phase reactant having carbonyl groups attached thereon, the ganglioside of interest linked to the modified solid-phase reactant by an amide bond between an amino group of the ganglioside of interest and a carbonyl group attached to the modified solid-phase reactant, and a control antigen linked to the modified solid-phase reactant;
   b) contacting the ganglioside modified solid-phase reactant with a test sample, thereby forming a contacted ganglioside modified solid-phase reactant;
   3) maintaining the contacted ganglioside modified solid-phase reactant under appropriate conditions to allow antibody to the ganglioside of interest, if present in the sample, to bind to the ganglioside of interest linked to the modified solid-phase reactant and to allow antibody to the control antigen, if present in the sample, to bind to the control antigen linked to the modified solid-phase reactant;
   d) determining the amount of antibody to the ganglioside of interest that is bound to the ganglioside of interest linked to the modified solid-phase reactant;
   e) determining the amount of antibody to the control antigen that is bound to the control antigen linked to the modified solid-phase reactant; and
   f) subtracting the amount of antibody to the control antigen from the amount of antibody to the ganglioside of interest, wherein the difference is equal to the amount of antibody specific to the ganglioside of interest.

19. The method of claim 18, wherein the ganglioside of interest is selected from the group consisting of: asialo GM ganglioside, GM1 ganglioside, GM2 ganglioside, GM3 ganglioside, GD1a ganglioside, GD1B ganglioside, GD2 ganglioside, GD3 ganglioside, GQ1b ganglioside, and GT1b ganglioside.

* * * * *